United States Patent
Zou et al.

(10) Patent No.: US 11,547,837 B2
(45) Date of Patent: Jan. 10, 2023

(54) DOUBLE-BALLOON CATHETER DEVICE FOR GASTROINTESTINAL ANASTOMOSIS

(71) Applicants: MICRO-TECH (NANJING) CO., LTD., Nanjing (CN); NANJING DRUM TOWER HOSPITAL, Nanjing (CN)

(72) Inventors: Xiaoping Zou, Nanjing (CN); Lei Wang, Nanjing (CN); Jianyu Wei, Nanjing (CN); Zhenghua Shen, Nanjing (CN); Jialing Sun, Nanjing (CN); Changqing Li, Nanjing (CN)

(73) Assignees: Micro-Tech (Nanjing) Co., Ltd.; Nanjing Drum Tower Hospital

( * ) Notice: Subject to any disclaimer, the term of this patent is extended or adjusted under 35 U.S.C. 154(b) by 457 days.

(21) Appl. No.: 16/761,766

(22) PCT Filed: Nov. 7, 2018

(86) PCT No.: PCT/CN2018/114375
§ 371 (c)(1),
(2) Date: May 5, 2020

(87) PCT Pub. No.: WO2019/091403
PCT Pub. Date: May 16, 2019

(65) Prior Publication Data
US 2020/0276420 A1 Sep. 3, 2020

(30) Foreign Application Priority Data
Nov. 7, 2017 (CN) .......................... 201721469557.5

(51) Int. Cl.
*A61M 25/10* (2013.01)
(52) U.S. Cl.
CPC .... *A61M 25/1011* (2013.01); *A61M 25/1025* (2013.01); *A61M 2025/1015* (2013.01);
(Continued)

(58) Field of Classification Search
CPC ...... A61M 25/1011; A61M 2025/1015; A61M 25/0662; A61M 2025/0681; A61B 17/12045
See application file for complete search history.

(56) References Cited

U.S. PATENT DOCUMENTS 5,456,694 A * 10/1995 Marin ..................... A61F 2/958
604/103.05
5,911,725 A * 6/1999 Boury .................... A61B 17/22
606/108

(Continued)

FOREIGN PATENT DOCUMENTS

CN 203291065 U 11/2013
CN 103561796 A 2/2014

(Continued)

OTHER PUBLICATIONS

International Search Report pertaining to PCT/CN2018/114375, 3 pages, Jan. 11, 2019.

*Primary Examiner* — Nathan R Price
*Assistant Examiner* — Courtney B Fredrickson
(74) *Attorney, Agent, or Firm* — Dinsmore & Shohl LLP

(57) ABSTRACT

A double-balloon catheter device for gastrointestinal anastomosis. The double-balloon catheter device for gastrointestinal anastomosis includes a liquid injection assembly, a double-balloon assembly, and a supporting device (15) connecting the liquid injection assembly and the double-balloon assembly. The liquid injection assembly includes a first balloon liquid injection connection port (2), a guide wire connection port (3), and a second balloon liquid injection connection port (4). The double-balloon assembly includes a double-balloon catheter device (5), and includes a first balloon (6) and a second balloon (7) that can expand-and that are respectively disposed on the two ends of the double-balloon catheter device (5). The double-balloon (Continued)

catheter device (5) is provided with a first balloon liquid injection channel (51), a guide wire channel (52), and a second balloon liquid injection channel (53).

21 Claims, 3 Drawing Sheets

(52) U.S. Cl.
CPC ............ *A61M 2025/1063* (2013.01); *A61M 2210/106* (2013.01)

(56) References Cited

U.S. PATENT DOCUMENTS

| | | | |
|---|---|---|---|
| 9,028,442 | B2 | 5/2015 | Solar et al. |
| 2001/0053920 | A1* | 12/2001 | Shaker ............... A61B 5/037 606/197 |
| 2006/0206064 | A1 | 9/2006 | Kagan et al. |

FOREIGN PATENT DOCUMENTS

| | | |
|---|---|---|
| CN | 103635212 A | 3/2014 |
| CN | 203710390 U | 7/2014 |
| CN | 106073844 A | 11/2016 |
| WO | 2012/103531 A2 | 8/2012 |

\* cited by examiner

DOUBLE-BALLOON CATHETER DEVICE FOR GASTROINTESTINAL ANASTOMOSIS

CROSS-REFERENCE TO RELATED APPLICATIONS

The present application is the National Phase entry of International Patent Application No. PCT/CN2018/114375 filed Nov. 7, 2018, which claims priority to Chinese Patent Application No. 201721469557.5, filed with the Chinese Patent Office on Nov. 7, 2017, entitled "Double-balloon Catheter Device for Gastrointestinal Anastomosis", the entire contents of both of which are incorporated herein by reference.

TECHNICAL FIELD

The present disclosure relates to the field of medical supplies, and in particular to a double-balloon catheter device for gastrointestinal anastomosis.

BACKGROUND ART

In the past, patients, who cannot stop vomiting upon the passage of food from the stomach into the intestinal tract is blocked due to invasion by tumors, either have to undergo laparotomy to establish a new passage between the stomach and the intestine, or have to be supported by intravenous nutrition. For those patients who are too old or whose body conditions are no longer suitable for laparotomy, the quality of life is extremely low, and a heavy burden is also placed on the family.

Gastrointestinal anastomosis is an operation in which a puncture is made into the proximal small intestine (the horizontal section of the duodenum) through the stomach using an ultrasound endoscope (endoscopic ultrasound, EUS), a guide wire is placed, and then a large-diameter fully-covered Lumen-apposing metal stent (LAMS) is placed under guidance to open up a passage between the stomach and the small intestine, namely, to recreate a new path between the stomach and the small intestine, so as to solve the impact of duodenal obstruction on patients' lives. In the past, the construction of such "bypass" requires laparotomy under general anesthesia, which may cause large trauma. A minimally invasive surgery using an endoscope causes less trauma, requires shorter surgery time, causes less pain, and allows faster recovery, which fully reflect the advantages of the endoscopic minimally invasive surgery. In recent years, with the continuous development, updating, and upgrading of the endoscopic technology and various equipment accessories, the endoscope has played a more and more important role in the diagnosis and treatment of various diseases of the digestive system. Especially the continuous innovation of the endoscopic minimally invasive surgery provides a new minimally invasive treatment method for many patients with gastrointestinal and biliary and pancreatic diseases who cannot or do not want to undergo surgery.

During puncture into the proximal small intestine through the stomach using an ultrasound endoscope, it is necessary to fix the proximal small intestine so that it is not displaceable, and at the same time it is necessary to make, in the proximal small intestine, a target point to be punctured by an EUS needle that can be detected by ultrasound endoscopy. The accurate positioning of the EUS needle cannot be achieved in the prior art, and only laparotomy or intravenous nutrition support can be performed.

SUMMARY

The object of the present disclosure includes, for example, providing a double-balloon catheter device for gastrointestinal anastomosis, which overcomes the shortcomings of the prior art, which is used in endoscopic gastrointestinal anastomosis surgery for serving the function of positioning an EUS needle and determining a target while also serving the function of fixing the proximal small intestine, which allows accurate positioning of the EUS needle and achieves a better surgical effect, and which has very good therapeutic effects on patients with duodenal obstruction caused by pancreatic cancer, pancreas head cancer, biliary tract cancer, or the like, and thus is a very promising treatment method.

The object of the present disclosure also includes providing a double-balloon catheter device for gastrointestinal anastomosis, which overcomes the shortcomings of the prior art, which is used in endoscopic gastrointestinal anastomosis surgery for serving the function of positioning an EUS needle and determining a target while also serving the function of fixing the proximal small intestine, and which allows accurate positioning of the EUS needle and achieves a better surgical effect.

Embodiments of the present disclosure may be implemented as follows:

An embodiment of the present disclosure provides a double-balloon catheter device for gastrointestinal anastomosis, which comprises a liquid injection assembly, a double-balloon assembly, and a supporting device connecting the liquid injection assembly and the double-balloon assembly;

wherein the liquid injection assembly comprises a first balloon liquid injection connection port, a guide wire connection port, and a second balloon liquid injection connection port;

the double-balloon assembly comprises a double-balloon catheter device and expandable first and second balloons disposed at the two ends of the double-balloon catheter device, respectively, the double-balloon catheter device is provided with a first balloon liquid injection channel, a guide wire channel, and a second balloon liquid injection channel, the first balloon liquid injection channel has an inlet connected to the first balloon liquid injection connection port and has an outlet connected to a liquid injection port of the first balloon, the second balloon liquid injection channel has an inlet connected to the second balloon liquid injection connection port and has an outlet connected to a liquid injection port of the second balloon, and the guide wire channel has an inlet connected to the guide wire connection port and has an outlet connected to a liquid outlet provided on the double-balloon catheter device between the first balloon and the second balloon, and the supporting device is connected to a first end portion of the double-balloon catheter device.

Optionally, the double-balloon catheter device for gastrointestinal anastomosis further comprises an introduction assembly configured to deliver the double-balloon catheter device into the gastrointestinal tract, the introduction assembly comprises a hose and a guide wire, and the hose is configured to accommodate the guide wire, the double-balloon assembly, and the supporting device.

Optionally, the hose may allow a gastroscope to pass therethrough, and is provided with a rapid-exchange connection port allowing the double-balloon catheter device and the guide wire to enter the interior of the hose.

Optionally, the first balloon liquid injection connection port, the guide wire connection port, and the second balloon liquid injection connection port are distributed in a misaligned manner inside the hose.

Optionally, the guide wire connection port is configured to be connected to an injection device.

Optionally, the hose has an outer diameter of a, and the hose has an inner diameter of b;

wherein 9.5 mm≤a≤25 mm, or a=13 mm; 9 mm≤b≤18 mm, or b=10.5 mm.

Optionally, the double-balloon catheter device is provided with at least one balloon tantalum mark, and the first balloon and/or the second balloon is each correspondingly provided with the balloon tantalum mark.

Optionally, the balloon tantalum mark comprises a first balloon tantalum mark and a second balloon tantalum mark; the first balloon tantalum mark is provided on a side of the first balloon close to and/or remote from the second balloon, and the second balloon tantalum mark is provided on a side of the second balloon close to and/or remote from the first balloon.

Optionally, the first balloon tantalum mark is provided on a side of the first balloon close to the second balloon, the second balloon tantalum mark is provided on a side of the second balloon remote from the first balloon, and the double-balloon catheter device is provided with a balloon catheter tip at its second end portion close to the second balloon.

Optionally, an intermediate balloon configured for positioning of puncture is further provided at the double-balloon catheter device between the first balloon and the second balloon, the liquid injection assembly further comprises a third balloon liquid injection connection port, the double-balloon catheter device is further provided with a third balloon liquid injection channel, an inlet of the third balloon liquid injection channel is connected to the third balloon liquid injection connection port, and an outlet of the third balloon liquid injection channel is connected to a liquid injection port of the intermediate balloon.

Optionally, the double-balloon catheter device has an outer diameter of c;

wherein 1.5 mm≤c≤4.5 mm, or c=2.3 mm.

Optionally, the first balloon and/or second balloon are configured to be expanded to have an outer diameter between 20 mm and 50 mm.

An embodiment of the present disclosure further provides a double-balloon catheter device for gastrointestinal anastomosis, which comprises: a liquid injection assembly, a supporting device, a double-balloon assembly, and an introduction assembly;

wherein the liquid injection assembly comprises a first balloon liquid injection connection port, a guide wire connection port, and a second balloon liquid injection connection port, the first balloon liquid injection connection port is connected to the supporting device by a first connection tube, the guide wire connection port is connected to the supporting device by a second connection tube, and the second balloon liquid injection connection port is connected to the supporting device by a third connection tube;

the double-balloon assembly comprises a double-balloon catheter device as well as a first balloon and a second balloon which are disposed at the double-balloon catheter device and which are expandable, and a first end portion of the double-balloon catheter device is connected to the supporting device;

the double-balloon catheter device is provided with a first balloon liquid injection channel, a guide wire channel, and a second balloon liquid injection channel, the first balloon liquid injection channel has an inlet communicating with the first connection tube and has an outlet communicating with a liquid injection port of the first balloon, the second balloon liquid injection channel has an inlet communicating with the third connection tube and has an outlet communicating with a liquid injection port of the second balloon, and the guide wire channel has an inlet communicating with the second connection tube and has an outlet communicating with a liquid outlet provided on the double-balloon catheter device between the first balloon and the second balloon;

the introduction assembly is configured to deliver the double-balloon catheter device into the gastrointestinal tract, the introduction assembly comprises a hose and a guide wire, and the hose is configured to accommodate the guide wire, the double-balloon assembly, and the supporting device.

Optionally, a second end portion of the double-balloon catheter device is provided with a balloon catheter tip, the second balloon is closer to the balloon catheter tip than the first balloon, and the first balloon is located between the first end portion and the second balloon.

Optionally, the hose is provided with a rapid-exchange connection port which is configured to allow introduction of a gastroscope, the double-balloon catheter device, and the guide wire into the interior of the hose.

Optionally, a balloon tantalum mark is provided on a side of the first balloon close to and/or remote from the second balloon, and a balloon tantalum mark is also provided on a side of the second balloon close to and/or remote from the first balloon.

Optionally, an intermediate balloon is further provided at the double-balloon catheter device between the first balloon and the second balloon, the liquid injection assembly further comprises a third balloon liquid injection connection port, the third balloon liquid injection connection port is connected to the supporting device by a fourth connection tube, the double-balloon catheter device is further provided with a third balloon liquid injection channel, an inlet of the third balloon liquid injection channel communicates with the fourth connection tube, and an outlet of the third balloon liquid injection channel communicates with a liquid injection port of the intermediate balloon.

Compared with the prior art, the embodiments of the present disclosure include, for example, the following advantageous effects:

A double-balloon catheter device for gastrointestinal anastomosis according to an embodiment of the present disclosure is used in endoscopic gastrointestinal anastomosis surgery for serving the function of positioning an EUS needle and determining a target while also serving the function of fixing the proximal small intestine, allows accurate positioning of the EUS needle, achieves a better surgical effect, has very good therapeutic effects on patients with duodenal obstruction caused by pancreatic cancer, pancreas head cancer, biliary tract cancer, or the like, and thus is a very promising treatment method.

A double-balloon catheter device for gastrointestinal anastomosis according to an embodiment of the present disclosure can be quickly introduced into the gastrointestinal tract by the introduction assembly and fix the gastrointestinal tract, which plays a role in positioning for anastomosis surgery, can be used conveniently without causing damage to patients, almost causes no pain during surgery, and thus is of great significance in clinical medicine.

BRIEF DESCRIPTION OF DRAWINGS

In order to more clearly illustrate technical solutions of embodiments of the present disclosure, drawings required for use in the embodiments will be described briefly below. It is to be understood that the drawings below are merely illustrative of some embodiments of the present disclosure, and therefore should not be considered as limiting its scope. It will be understood by those of ordinary skill in the art that other relevant drawings can also be obtained from these drawings without any inventive effort.

Figure 1:
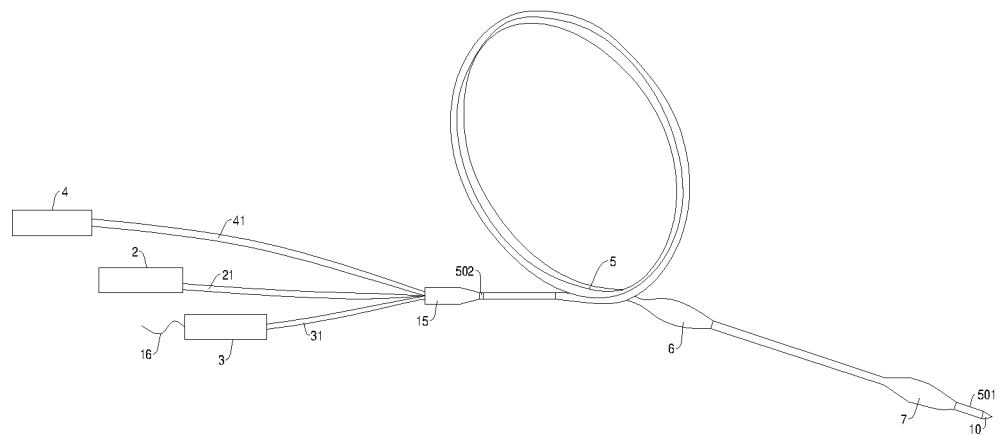
FIG. 1 is a schematic structural diagram of a double-balloon catheter device for gastrointestinal anastomosis according to an embodiment of the present disclosure.

Reference Numerals: 1-hose; 2-first balloon liquid injection connection port; 21-first connection tube; 3-guide wire connection port; 31-second connection tube; 4-second balloon liquid injection connection port; 41-third connection tube; 5-double-balloon catheter device; 51-first balloon liquid injection channel; 52-guide wire channel; 53-second balloon liquid injection channel; 54-third balloon liquid injection channel; 501-second end portion; 502-first end portion; 6-first balloon; 7-second balloon; 8-first balloon tantalum mark; 9-second balloon tantalum mark; 10-balloon catheter tip; 11-rapid-exchange connection port; 12-liquid outlet; 13-intermediate balloon; 14-third balloon liquid injection connection port; 141-fourth connection tube; 15-supporting device; 16-guide wire.

DETAILED DESCRIPTION OF EMBODIMENTS

Exemplary embodiments, features, and aspects of the present disclosure will be described below in detail with reference to the accompanying drawings. The same reference numerals in the drawings represent elements with the same or similar function. Although various aspects of the embodiments are shown in the drawings, the drawings are not necessarily drawn to scale unless specifically noted.

In order to further clarify the objects, technical solutions, and advantages of the embodiments of the present disclosure, the technical solutions of the embodiments of the present disclosure will be described below clearly and completely with reference to the drawings of the embodiments of the present disclosure. It is apparent that the embodiments to be described are some, but not all of the embodiments of the present disclosure. Generally, the components of the embodiments of the present disclosure, as described and illustrated in the drawings herein, may be arranged and designed in a wide variety of different configurations.

Thus, the following detailed description of the embodiments of the present disclosure, as represented in the drawings, is not intended to limit the scope of the present disclosure as claimed, but is merely representative of selected embodiments of the present disclosure. All the other embodiments obtained by those of ordinary skill in the art in light of the embodiments of the present disclosure without inventive efforts will fall within the scope of the present disclosure as claimed.

It should be noted that similar reference numerals and letters refer to similar items in the following drawings, and thus once a certain item is defined in one figure, it may not be further defined or explained in the following figures.

In the description of the present disclosure, it should be noted that orientation or positional relationships indicated by the terms such as "center", "up", "down", "left", "right", "vertical", "horizontal", "inside", and "outside", if present, are the orientation or positional relationships shown based on the drawings, or the orientation or positional relationships in which the inventive product is conventionally placed in use, and these terms are intended only to facilitate the description of the present disclosure and simplify the description, but not intended to indicate or imply that the referred devices or elements must be in a particular orientation, or constructed or operated in the particular orientation, and therefore should not be construed as limiting the present disclosure.

In addition, terms such as "first", "second", and "third", if present, are used for distinguishing the description only, and should not be understood as an indication or implication of relative importance.

In addition, the term "horizontal", "vertical", "overhanging", or the like, if present, does not mean that a component is required to be absolutely horizontal or overhanging, but means that the component may be slightly inclined. For example, by the term "horizontal", it is simply meant that its direction is more horizontal than the term "vertical", and it is not meant that the structure must be completely horizontal, but it is meant that the structure may be slightly inclined.

In the description of the present disclosure, it should also be noted that terms such as "disposed", "mounted", "coupled", and "connected", if present, should be understood broadly unless otherwise expressly specified or defined. For example, connection may be fixed connection or detachable connection or integral connection, may be mechanical connection or electric connection, or may be direct coupling or indirect coupling via an intermediate medium or internal communication between two elements. The specific meanings of the above-mentioned terms in the present disclosure can be understood by those of ordinary skill in the art according to specific situations.

It should be noted that the features in the embodiments of the present disclosure may be combined with each other without conflict.

Referring to FIGS. 1 to 5, this embodiment provides a double-balloon catheter device 5 for gastrointestinal anastomosis, which comprises a liquid injection assembly, a double-balloon assembly, and a supporting device 15 connecting the liquid injection assembly and the double-balloon assembly;

wherein the liquid injection assembly comprises a first balloon liquid injection connection port 2, a guide wire connection port 3, and a second balloon liquid injection connection port 4;

the double-balloon assembly comprises a double-balloon catheter device 5 and expandable first and second balloons 6 and 7 disposed at the two ends of the double-balloon catheter device 5, respectively, the double-balloon catheter device 5 is provided with a first balloon liquid injection channel 51, a guide wire channel 52, and a second balloon liquid injection channel 53, an inlet of the first balloon liquid injection channel 51 is connected to the first balloon liquid injection connection port 2, an outlet of the first balloon liquid injection channel 51 is connected to a liquid injection port of the first balloon 6, an inlet of the second balloon liquid injection channel 53 is connected to the second balloon liquid injection connection port 4, an outlet of the second balloon liquid injection channel 53 is connected to a liquid injection port of the second balloon 7, an inlet of the guide wire channel 52 is connected to the guide wire connection port 3, and an outlet of the guide wire channel 52 is connected to a liquid outlet 12 provided on the double-balloon catheter device 5 between the first balloon 6 and the second balloon 7, and the supporting device 15 is connected to a first end portion 502 of the double-balloon catheter device 5.

In general, after the double-balloon assembly is inserted into a human body through an oral cavity, the first balloon 6 is relatively close to the oral cavity, and the second balloon 7 is relatively far away from the oral cavity. Namely, it can be understood that the first balloon 6 is a proximal balloon, and the second balloon 7 is a distal balloon. Moreover, the first end portion 502 of the double-balloon catheter device 5 is a proximal end, the second end portion 501 of the double-balloon catheter device is a distal end, and an opening of the second end portion 501 is configured to allow a guide wire 16 to pass therethrough.

In one mode, the first end portion 502 and the supporting device 15 are molded integrally by an injection molding process. After the supporting device 15 is inserted into the human body, it can play a certain role in supporting, and also serves to stably connect the liquid injection assembly and the double-balloon catheter device 5.

When a liquid is injected through the first balloon liquid injection connection port 2, the liquid passes through the first balloon liquid injection channel 51 and enters the first balloon 6 via the liquid injection port of the first balloon 6, and the first balloon 6 is filled with the liquid and then is expanded. When a liquid is injected through the second balloon liquid injection connection port 4, the liquid passes through the second balloon liquid injection channel 53 and enters the second balloon 7 via the liquid injection port of the second balloon 7, and the second balloon 7 is filled with the liquid and then is expanded. After the two balloons are expanded, they are in contact with the inner wall of the intestine and are fixed relative to the intestine. When the guide wire 16 is introduced from the guide wire connection port 3 and protrudes from the opening of the second end portion 501 via the guide wire channel 52, it is convenient to guide the double-balloon catheter device 5. Meanwhile, when a liquid is injected into the guide wire connection port 3, the liquid may flow out of the liquid outlet 12 via the guide wire channel 52. The outflowing liquid can be observed by ultrasound endoscopy so that the positioning of an EUS needle in a gastrointestinal anastomosis surgery can be carried out, and a target can be determined. Therefore, the guide wire channel 52 may be shared as a lumen by the guide wire 16 and the liquid required to be injected, whereby the outer diameter of the entire device can be reduced to a certain extent, so that the device can pass through a smaller stenosis.

The double-balloon catheter device for gastrointestinal anastomosis is used in endoscopic gastrointestinal anastomosis surgery for serving the function of positioning an EUS needle and determining a target while also serving the function of fixing the proximal small intestine, allows accurate positioning of the EUS needle, achieves a better surgical effect, has very good therapeutic effects on patients with duodenal obstruction caused by pancreatic cancer, pancreas head cancer, biliary tract cancer, or the like, and thus is a very promising treatment method.

Optionally, the double-balloon catheter device for gastrointestinal anastomosis further comprises an introduction assembly configured to deliver the double-balloon catheter device 5 into the gastrointestinal tract, the introduction assembly comprises a hose 1 and a guide wire 16, and the hose 1 is configured to accommodate the guide wire 16, the double-balloon assembly, and the supporting device 15.

The hose 1 has a larger diameter and can also accommodate a gastroscope. The hose 1 and the guide wire 16 are delivered to the proximal end of the stenosis by gastroscopic monitoring, and the guide wire 16 further passes through the stenosed section into the proximal small intestine. The gastroscope is withdrawn and is exchanged with a double-balloon catheter instrument. While being supported by the hose 1, the double-balloon catheter device 5 is guided by the guide wire 16 into the proximal small intestine through the stenosed section of the duodenum.

Figure 2:
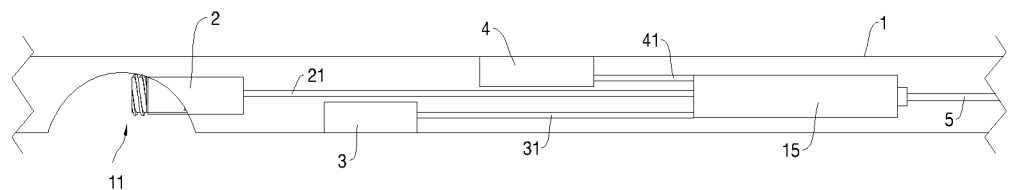
FIG. 2 is a schematic structural diagram of a liquid injection assembly according to an embodiment of the present disclosure.

With reference to FIG. 2, optionally, the hose 1 may allow a gastroscope to pass therethrough, and is provided with a rapid-exchange connection port 11 allowing the double-balloon catheter device 5 and the guide wire 16 to enter the interior of the hose 1.

The rapid-exchange connection port 11 is provided in a side wall of the hose 1. A device required to be inserted into a human body can be conveniently and easily inserted into the interior of the human body via the hose 1 through the rapid-exchange connection port 11. Meanwhile, the distal end of the hose 1 may also be used as a handle allowing a user to manually guide the hose 1 into the interior of the human body.

Figure 3:
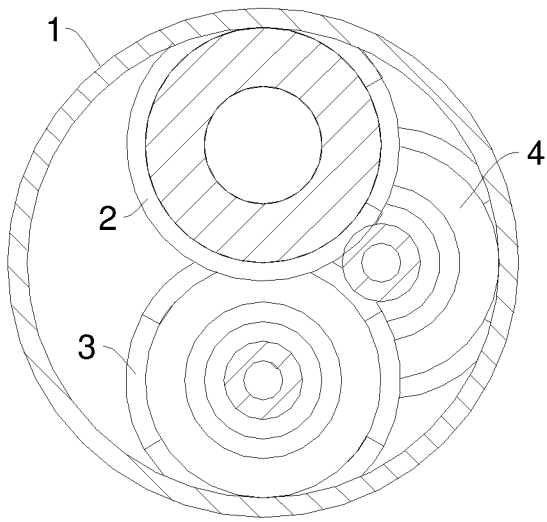
FIG. 3 is a schematic cross-sectional structural diagram of a hose.

With reference to FIG. 2 and FIG. 3, optionally, the first balloon liquid injection connection port 2, the guide wire connection port 3, and the second balloon liquid injection connection port 4 are distributed in a misaligned manner inside the hose 1.

It should be noted that, in a specific implementation, two of the connection ports or the three connection ports may be distributed side by side.

Optionally, the guide wire connection port 3 is configured to be connected to an injection device.

The injection device may be selected from a normal saline injection device, which is configured to inject normal saline. Of course, other medical injection devices may also be selected and used. It should be noted that the guide wire connection port 3 may have two inlets. In other words, the guide wire 16 can be threaded therethrough while normal saline is injected thereinto.

Optionally, the hose 1 has an outer diameter of a, and the hose 1 has an inner diameter of b;

wherein 9.5 mm≤a≤25 mm, or a=13 mm; 9 mm≤b≤18 mm, or b=10.5 mm.

It should be noted that, in a specific implementation, a may be selected from 9.5 mm, 11 mm, 13 mm, 17 mm, 20 mm, 25 mm, or the like, and b may be selected from 9 mm, 10.5 mm, 16 mm, 18 mm, or the like.

Figure 4:
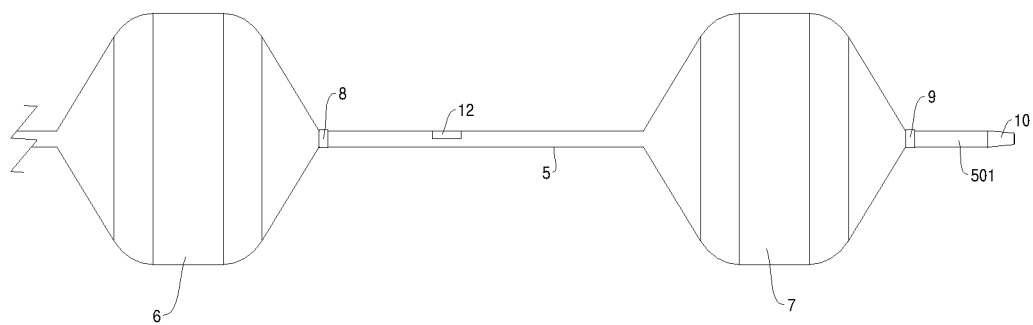
FIG. 4 is a schematic structural diagram of a double-balloon catheter device of FIG. 1.

With reference to FIG. 4, optionally, the double-balloon catheter device 5 is provided with at least one balloon tantalum mark, and the first balloon 6 and/or the second balloon 7 is each correspondingly provided with the balloon tantalum mark.

The balloon tantalum mark can be clearly seen to be developed under X-ray development, thus the balloon tantalum mark can be used for positioning. In general, both of the balloons are provided with the balloon tantalum marks in order to determine the positions of both of the balloons. When only one balloon is provided with the balloon tantalum mark, the balloon tantalum mark is generally selected to be provided on the distal balloon (the second balloon 7).

Optionally, the balloon tantalum mark comprises a first balloon tantalum mark 8 and a second balloon tantalum mark 9; the first balloon tantalum mark 8 is provided on a side of the first balloon 6 close to and/or remote from the second balloon 7, and the second balloon tantalum mark 9 is provided on a side of the second balloon 7 close to and/or remote from the first balloon 6.

With reference to FIG. 4, in general, the balloon tantalum mark is provided on the double-balloon catheter device 5 and is located on the left and/or right side of the balloon, and, of course, may also be provided on the double-balloon catheter device 5 between the two balloons.

In one mode, the first balloon tantalum mark 8 is provided on a side of the first balloon 6 close to the second balloon 7, the second balloon tantalum mark 9 is provided on a side of the second balloon 7 remote from the first balloon 6, and the double-balloon catheter device 5 is provided with a balloon catheter tip 10 at the second end portion 501 close to the second balloon 7.

The second balloon tantalum mark 9 is provided on a side of the second balloon 7 remote from the first balloon 6. When the double-balloon catheter device 5 has just been introduced into the human body, a developer is not injected into the balloon. The mark is placed at the distal end of the distal balloon and at a shorter distance from the balloon catheter tip 10. Therefore, if the position of the second balloon tantalum mark 9 is determined, the position of the balloon catheter tip 10 can be substantially determined.

Figure 6:
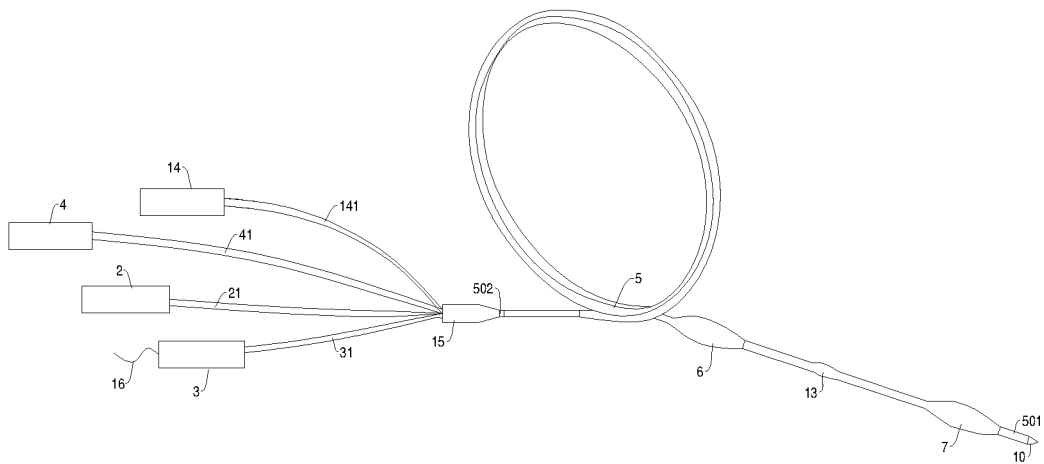
FIG. 6 is a schematic structural diagram of another double-balloon catheter device for gastrointestinal anastomosis according to an embodiment of the present disclosure.
Figure 7:
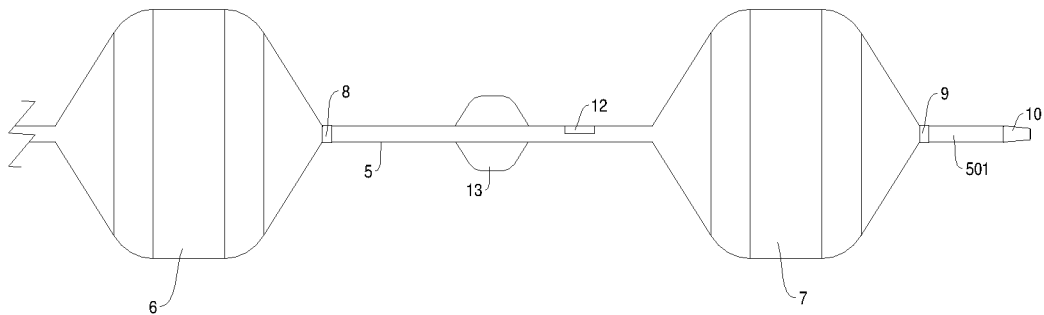
FIG. 7 is a schematic structural diagram of a double-balloon catheter device of FIG. 6.
Figure 8:
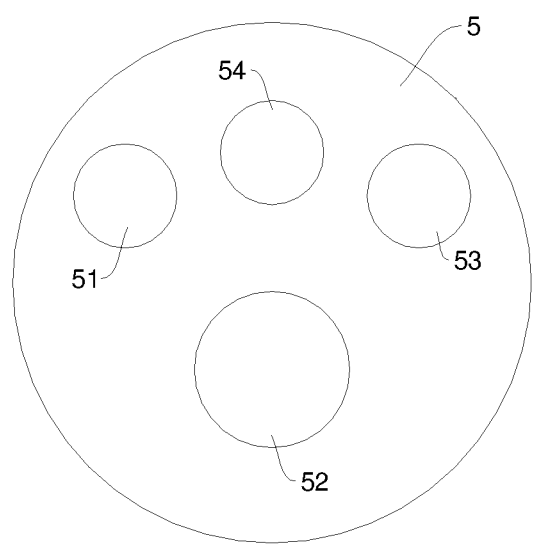
FIG. 8 is a schematic cross-sectional structural diagram of the double-balloon catheter device of FIG. 7.

Referring to FIGS. 6 to 8, optionally, an intermediate balloon 13 configured for positioning of puncture is further provided at the double-balloon catheter device 5 between the first balloon 6 and the second balloon 7, the liquid injection assembly further comprises a third balloon liquid injection connection port 14, the double-balloon catheter device 5 is further provided with a third balloon liquid injection channel 54, an inlet of the third balloon liquid injection channel 54 is connected to the third balloon liquid injection connection port 14, and an outlet of the third balloon liquid injection channel 54 is connected to a liquid injection port of the intermediate balloon 13.

When a liquid is injected into the third balloon liquid injection channel 54 through the third balloon liquid injection connection port 14, the liquid enters the intermediate balloon 13 via the liquid injection port of the intermediate balloon 13. A slight flow of the liquid in the intermediate balloon 13 can be observed on a screen of the ultrasound endoscope (EUS). The intermediate balloon 13 can also be used for positioning.

Optionally, the double-balloon catheter device 5 has an outer diameter of c;

wherein 1.5 mm≤c≤4.5 mm, or c=2.3 mm.

It should be noted that c may be selected from 1.5 mm, 1.7 mm, 2.3 mm, 2.8 mm, 3.5 mm, 4.5 mm, or the like.

Optionally, the first balloon 6 and/or second balloon 7 are configured to be expanded to have an outer diameter between 20 mm and 50 mm.

It should be noted that the expanded two balloons should not have too large or too small outer diameters, which may cause discomfort to the patient in the case of too large outer diameters, and may not be effectively and stably fixed relative to the inner wall of the intestine in the case of too small outer diameters. In general, the first balloon 6 and the second balloon 7 each having an expanded outer diameter of 20 mm, 25 mm, 30 mm, 35 mm, 40 mm, 45 mm, 50 mm, or the like may be selected and used.

Referring to FIGS. 1 to 5, this embodiment further provides a double-balloon catheter device for gastrointestinal anastomosis, which comprises a liquid injection assembly, a supporting device 15, a double-balloon assembly, and an introduction assembly;

wherein the liquid injection assembly comprises a first balloon liquid injection connection port 2, a guide wire connection port 3, and a second balloon liquid injection connection port 4, the first balloon liquid injection connection port 2 is connected to the supporting device 15 by a first connection tube 21, the guide wire connection port 3 is connected to the supporting device 15 by a second connection tube 31, and the second balloon liquid injection connection port 4 is connected to the supporting device 15 by a third connection tube 41;

the double-balloon assembly comprises a double-balloon catheter device 5 as well as a first balloon 6 and a second balloon 7 which are disposed at the double-balloon catheter device 5 and which are expandable, and a first end portion 502 of the double-balloon catheter device 5 is connected to the supporting device 15;

the double-balloon catheter device 5 is provided with a first balloon liquid injection channel 51, a guide wire channel 52, and a second balloon liquid injection channel 53, an inlet of the first balloon liquid injection channel 51 communicates with the first connection tube 21, an outlet of the first balloon liquid injection channel 51 communicates with a liquid injection port of the first balloon 6, an inlet of the second balloon liquid injection channel 53 communicates with the third connection tube 41, an outlet of the second balloon liquid injection channel 53 communicates with a liquid injection port of the second balloon 7, an inlet of the guide wire channel 52 communicates with the second connection tube 31, and an outlet of the guide wire channel 52 communicates with a liquid outlet 12 provided on the double-balloon catheter device 5 between the first balloon 6 and the second balloon 7;

the introduction assembly is configured to deliver the double-balloon catheter device 5 into the gastrointestinal tract, the introduction assembly comprises a hose 1 and a guide wire 16, and the hose 1 is configured to accommodate the guide wire 16, the double-balloon assembly, and the supporting device 15.

The double-balloon catheter device for gastrointestinal anastomosis can be quickly introduced into the gastrointestinal tract by the introduction assembly and fix the gastrointestinal tract, which plays a role in positioning for anastomosis surgery, can be used conveniently without causing damage to patients, almost causes no pain during surgery, and thus is of great significance in clinical medicine.

Optionally, a second end portion 501 of the double-balloon catheter device 5 is provided with a balloon catheter tip 10, the second balloon 7 is closer to the balloon catheter tip 10 than the first balloon 6, and the first balloon 6 is located between the first end portion 502 and the second balloon 7.

The second balloon 7 is disposed adjacent to the balloon catheter tip 10. Upon the position of the second balloon 7 is determined, the position of the balloon catheter tip 10 can be determined. The guide wire 16 may be protruded from the balloon catheter tip 10 via the guide wire channel 52 through the guide wire connection port 3, to serve the function of guiding the double-balloon catheter device 5.

Optionally, the hose 1 is provided with a rapid-exchange connection port 11 which is configured to allow introduce of a gastroscope, the double-balloon catheter device 5, and the guide wire 16 into the interior of the hose 1.

The rapid-exchange connection port 11 is provided in a side wall of the hose 1 so that the gastroscope, the double-balloon catheter device 5, and the guide wire 16 can be introduced into the interior of a human body through the hose 1.

Optionally, a balloon tantalum mark is provided on a side of the first balloon 6 close to and/or remote from the second balloon 7, and a balloon tantalum mark is also provided on a side of the second balloon 7 close to and/or remote from the first balloon 6.

The balloon tantalum mark can be clearly seen to be developed under X-ray development, thus the balloon tantalum mark can be used for positioning. In general, both of the balloons are provided with the balloon tantalum marks in order to determine the positions of both of the balloons.

With reference to FIGS. 6 to 8, optionally, an intermediate balloon 13 is further provided at the double-balloon catheter device 5 between the first balloon 6 and the second balloon 7, the liquid injection assembly further comprises a third balloon liquid injection connection port 14, the third balloon liquid injection connection port 14 is connected to the supporting device 15 by a fourth connection tube 141, the double-balloon catheter device 5 is further provided with a third balloon liquid injection channel 54, an inlet of the third balloon liquid injection channel 54 communicates with the fourth connection tube 141, and an outlet of the third balloon liquid injection channel 54 communicates with a liquid injection port of the intermediate balloon 13.

A liquid can be stably and effectively injected into the intermediate balloon 13 through the third balloon liquid injection connection port 14 provided separately.

In an implementation mode, as shown in FIGS. 1 to 5, a double-balloon catheter device for gastrointestinal anastomosis according to this embodiment consists of a hose 1 provided with a rapid-exchange connection port 11, a first balloon liquid injection connection port 2, a guide wire connection port 3, a second balloon liquid injection connection port 4, a double-balloon catheter device 5, a first balloon 6, a second balloon 7, a first balloon tantalum mark 8, a second balloon tantalum mark 9, and a balloon catheter tip 10. The first balloon 6 is a proximal balloon, i.e., a balloon close to the oral cavity, and the second balloon 7 is a distal balloon, i.e., a balloon relatively far away from the oral cavity.

The first balloon liquid injection connection port 2, the guide wire connection port 3, and the second balloon liquid injection connection port 4 constitute a liquid injection assembly. The first balloon 6 and the second balloon 7 are disposed at the two ends of the double-balloon catheter device 5 such that a double-balloon assembly is formed. The first balloon tantalum mark 8 is provided on a side of the first balloon 6 close to the second balloon 7, and the second balloon tantalum mark 9 is provided on a side of the second balloon 7 remote from the first balloon 6. An end of the double-balloon catheter device 5 close to the second balloon 7 is a second end portion 501, and the second end portion 501 is provided with a balloon catheter tip 10. The hose 1, and the guide wire 16 serving to guide the double-balloon catheter device 5 constitute an introduction assembly. When in use, the double-balloon assembly is introduced into the gastrointestinal tract, and the liquid injection assembly is located outside the oral cavity. The first balloon liquid injection connection port 2, the guide wire connection port 3, and the second balloon liquid injection connection port 4 in FIG. 2 are all located outside the rapid-exchange connection port 11 during operation. The liquid injection assembly and the double-balloon assembly are connected by a supporting device 15. The first end portion 502 of the double-balloon catheter device 5 is connected to the supporting device 15, and the first end portion 502 is molded integrally with the supporting device 15 by using injection molding.

Moreover, each of the first balloon 6 and the second balloon 7 is provided with a liquid injection port.

With reference to FIG. 4, a liquid outlet 12 is provided on a part of the double-balloon catheter device 5 located between the first balloon 6 and the second balloon 7.

With reference to FIG. 2, the first balloon liquid injection connection port 2, the guide wire connection port 3, and the second balloon liquid injection connection port 4 are distributed in a misaligned manner inside the hose 1, and therefore can sequentially pass through the inside of the hose 1.

A first balloon liquid injection channel 51, a guide wire channel 52, and a second balloon liquid injection channel 53 are disposed inside the double-balloon catheter device 5.

An inlet of the first balloon liquid injection channel 51 is connected to the first balloon liquid injection connection port 2, an outlet of the first balloon liquid injection channel 51 is connected to the liquid injection port of the first balloon 6, an inlet of the second balloon liquid injection channel 53 is connected to the second balloon liquid injection connection port 4, an outlet of the second balloon liquid injection channel 53 is connected to the liquid injection port of the second balloon 7, an inlet of the guide wire channel 52 is connected to the guide wire connection port 3, and an outlet of the guide wire channel 52 is connected to a liquid outlet 12 provided on the double-balloon catheter device 5 between the first balloon 6 and the second balloon 7. The guide wire connection port 3 is also connected to a normal saline injection device, which is configured to inject normal saline.

In another implementation mode, as shown in FIGS. 6 to 8, the double-balloon assembly is further provided, between the first balloon 6 and the second balloon 7, with an intermediate balloon 13 configured for positioning. After the first balloon 6 and the second balloon 7 are placed at predetermined positions in the intestinal tract, a developer is injected sequentially into the second balloon liquid injection connection port 4 and the first balloon liquid injection connection port 2 such that the second balloon 7 and the first balloon 6 are expanded sequentially, respectively, in order to fix the targeted proximal small intestine in the intestinal tract to prevent its free movement or peristalsis. Then, a liquid is injected into the intermediate balloon 13 through the third balloon liquid injection connection port 14 so that the doctor can perform positioning based on the intermediate balloon 13.

The operating principle of the double-balloon catheter device for gastrointestinal anastomosis according to this embodiment will be further explained below:

A gastroscope is threaded thereinto from the rapid-exchange connection port 11 of the hose 1, and the gastroscope is covered by an outer tube for the gastroscope. The hose 1 and the gastroscope assembly are passed into the obstructed portion of the duodenum through the esophagus and stomach via the mouth, and then a first zebra guide wire is threaded via a forceps channel hole of the gastroscope, and the first zebra guide wire is passed into the proximal small intestine and the small intestine through the site of obstruction and stenosis in the duodenum and is held in place. The gastroscope is withdrawn from the rapid-exchange connection port 11 of the hose 1, and then the double-balloon catheter device 5 is inserted from the rapid-exchange connection port 11 of the hose 1 along the first zebra guide wire of 0.89 mm and passed into the proximal small intestine through the site of obstruction and stenosis in the duodenum. The first balloon tantalum mark 8 and the second balloon tantalum mark 9 can be clearly seen to be developed under X-ray development. The double-balloon catheter device 5 is dragged such that the first balloon 6 and the second balloon 7 are placed at predetermined positions in the intestinal tract. A developer is injected sequentially into the second balloon liquid injection connection port 4 and the first balloon liquid injection connection port 2, so that the second balloon 7 and the first balloon 6 are expanded sequentially, respectively, in order to fix the targeted proximal small intestine in the intestinal tract to prevent its free movement or peristalsis, in preparation for subsequent accurate puncture using an EUS needle.

After the double-balloon catheter device 5 is placed in such a manner that it is fixed by the first balloon 6 and the second balloon 7, the hose 1 is slowly withdrawn from the rapid-exchange connection port 11, the first zebra guide wire of 0.89 mm and the double-balloon catheter device 5 sleeved thereon are left in the body through the duodenum, and at the same time, the first balloon 6 and the second balloon 7 are both inflated and in an operating state.

An ultrasound endoscope (EUS) is passed into the bottom of the stomach via the mouth. The positions of the first balloon 6 and the second balloon 7 are observed using the ultrasound endoscope (EUS), and at the same time, normal saline is injected through the guide wire connection port 3 such that the normal saline flows out from the liquid outlet 12 between the first balloon 6 and the second balloon 7. Alternatively, an intermediate balloon 13 may be provided between the first balloon 6 and the second balloon 7, and the position to be punctured may be determined by the intermediate balloon 13. On the screen of the ultrasound endoscope (EUS), the normal saline flowing out of the liquid outlet 12 can be observed, and a slight flow of the liquid in the intermediate balloon 13 can also be observed. Generally, in the actual operation, the doctor makes a puncture while aiming at a clearly visible structure, and, in general, makes a puncture while aiming at the second balloon 7 (distal balloon). The two balloons have separate liquid injection channels. In this way, even if the second balloon 7 is damaged, the first balloon 6 is effective to ensure firm holding of the intestinal tract by the first balloon 6 in the subsequent operation so as to ensure a stable position of the entire structure. Generally, it should be at least ensured that the inflated first balloon 6 has an outer diameter between 20 mm and 50 mm, so that the inflated first balloon 6 can firmly fix the proximal small intestine, to guarantee no displacement of the proximal small intestine during the subsequent puncture into the proximal small intestine from the stomach using the ultrasound endoscope (EUS), thereby ensuring successful puncture and successful release of a stent.

After the position of the liquid outlet 12 or the intermediate balloon 13 is determined, a 19G EUS puncture needle punctures directly and accurately into the proximal small intestine from the bottom of the stomach through the forceps channel of the ultrasound endoscope, and a second zebra guide wire is allowed to directly reach the proximal small intestine along an inner hole of the 19G puncture needle. The 19G puncture needle is withdrawn, and a stent implanter is introduced directly into the proximal small intestine via the stomach along the second guide wire. In this embodiment, the stent implanter is may be a nickel-titanium stent implanter. A lumen-apposing metal stent in the stent implanter is released in the proximal small intestine at its distal end and is released in the stomach at its proximal end. In this way, a passage is established between the stomach and the proximal small intestine for anastomosis of the stomach and the intestine. This has very good therapeutic effects on patients with duodenal obstruction caused by pancreatic cancer, pancreas head cancer, biliary tract cancer, or the like, and is a very promising treatment method. The double-balloon catheter device for gastrointestinal anastomosis according to this embodiment serves the function of positioning an EUS needle and determining a target and can also serve the function of fixing the proximal small intestine during surgery.

It should be noted that, in a patient with duodenal stenosis, a natural cavity or lumen is compressed by tumor and thus blocked, in which substantially no gap is shown endoscopically, through which an ordinary instrument is generally not allowed to pass, and through which, in general, only a 0.89 mm guide wire and a 2.3 mm (7 Fr) contrast catheter and a 2.3 mm (7 Fr) balloon catheter are allowed to pass. Therefore, the double-balloon catheter device 5 having a smaller outer diameter is more likely to pass through the stenosed area to ensure successful surgery. The double-balloon design in FIG. 1 is used to meet the independent control of the two balloons, and additionally the guide wire cavity and the liquid injection cavity are merged to ensure the functions of injecting a liquid in the middle space of the two balloons and passing the guide wire. The entire double-balloon catheter has only three cavities, so that the catheter can be made to have an outer diameter of 2.3 mm (7 Fr), and thus the catheter is allowable to pass through a stenosed area more easily.

After the gastroscope and the hose 1 are withdrawn, only the double-balloon catheter device 5 with expanded balloons is left. The double-balloon catheter device 5 located in the esophagus and stomach has an outer diameter of 2.3 mm (7 Fr), which provides space for subsequent treatment using the ultrasound endoscope (EUS) (with an outer diameter of 13 mm). In this case, the total outer diameter is 15.3 mm, which is acceptable to the esophagus of the patient.

The balloon may be pierced during puncture from the stomach into the proximal small intestine using an ultrasound endoscope. Also, after a puncture is made using one of the balloons as a target point, when a second guide wire is placed according to the operation requirements, the distal balloon acting as the target point may be pierced. The two balloons have separate liquid injection channels, and thus the other balloon (proximal balloon) can continue achieving the supporting and dragging effects, to play a role in fixing the intestinal tract during the subsequent placement of a lumen-apposing metal stent of an implanter. Otherwise, the intestine will be freely moved in the abdominal cavity, and the stent cannot be released successfully.

In order to pass through a hard lesion of stenosis, an instrument is required to have a diameter as small as possible. When introduced through the curved stomach into the duodenum and reaching the proximal small intestine, this instrument is required to have a length of at least 1.2 meters from the mouth to the proximal small intestine at its part introduced into the human body, plus an external operating distance, and therefore this instrument has a total length of 1.8 to 2.3 meters. Although the thin and long instrument is being supported by the guide wire 16 while being delivered toward the target position along the guide wire 16 acting equivalently to a track, the guide wire 16 is not rigid, thus the catheter can hardly be successfully inserted when passing through the curve of the stomach and the stenosed portion of the duodenum, which may easily cause failure of surgery. In this embodiment, the hose 1 is introduced into the human body along with the endoscope in the early stage, and the distal end of the hose 1 is placed on the side of proximal end of the stenosed portion of the duodenum, which supports the double-balloon catheter device 5 from the mouth to the duodenum, which is one of the key factors for successful surgery. The time taken for delivery of the double-balloon catheter device 5 into the proximal small intestine after the withdrawal of the endoscope is greatly shortened.

In Some Embodiments

Referring to FIG. 1, the double-balloon catheter device for gastrointestinal anastomosis shown in FIG. 1 comprises a first balloon liquid injection connection port 2, a guide wire connection port 3, a second balloon liquid injection connection port 4, a guide wire 16, a first connection tube 21, a second connection tube 31, a third connection tube 41, a supporting device 15, a double-balloon catheter device 5, a first balloon 6, and a second balloon 7; the first balloon liquid injection connection port 2 is connected to the supporting device 15 by the first connection tube 21, the second balloon liquid injection connection port 4 is connected to the supporting device 15 by the third connection tube 41, and the guide wire connection port 3 is connected to the supporting device 15 by the second connection tube 31; the two ends of the double-balloon catheter device 5 are a first end portion 502 and a second end portion 501, respectively, the first end portion 502 is connected to the supporting device 15, and the second end portion 501 is provided with a balloon catheter tip 10; the first balloon 6 and the second balloon 7 are disposed at the double-balloon catheter device 5, and the second balloon 7 is disposed adjacent to the balloon catheter tip 10, and the first balloon 6 is located between the first end portion 502 and the second balloon 7.

Referring to FIG. 2 and FIG. 3, the first balloon liquid injection connection port 2, the guide wire connection port 3, the second balloon liquid injection connection port 4, the first connection tube 21, the second connection tube 31, the third connection tube 41, the supporting device 15, and the double-balloon catheter device 5 shown in FIG. 2 and FIG. 3 are all accommodated in a hose 1; a rapid-exchange connection port 11 is provided in a side wall of the hose 1; and the first balloon liquid injection connection port 2, the guide wire connection port 3, the second balloon liquid injection connection port 4, the first connection tube 21, the second connection tube 31, the third connection tube 41, the supporting device 15, and the double-balloon catheter device 5 are all introduced into the interior of the hose 1 through the rapid-exchange connection port 11.

Figure 5:
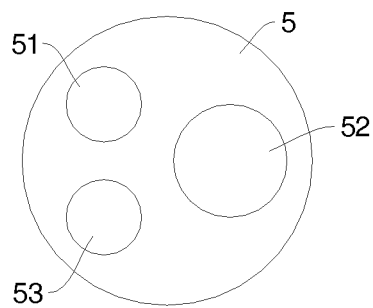
FIG. 5 is a schematic cross-sectional structural diagram of the double-balloon catheter device of FIG. 4.

Referring to FIG. 4 and FIG. 5, the double-balloon catheter device 5 shown in FIG. 4 is provided with a first balloon 6 and a second balloon 7, and a first balloon tantalum mark 8 is provided on a side of the first balloon 6 close to the second balloon 7, a second balloon tantalum mark 9 is provided on a side of the second balloon 7 remote from the first balloon 6, and the second end portion 501 of the double-balloon catheter device 5 is provided with a balloon catheter tip 10; the double-balloon catheter device 5 is further provided with a liquid outlet 12, which is located between the first balloon 6 and the second balloon 7; the first balloon 6 communicates with the first balloon liquid injection connection port 2 through a first balloon liquid injection channel 51 provided in the double-balloon catheter device 5, the second balloon 7 communicates with the second balloon liquid injection connection port 4 through a second balloon liquid injection channel 53 provided in the double-balloon catheter device 5, and the liquid outlet 12 communicates with the guide wire connection port 3 through a guide wire channel 52 provided in the double-balloon catheter device 5.

Referring to FIG. 6, the double-balloon catheter device for gastrointestinal anastomosis shown in FIG. 6 comprises a first balloon liquid injection connection port 2, a guide wire connection port 3, a second balloon liquid injection connection port 4, a guide wire 16, a third balloon liquid injection connection port 14, a first connection tube 21, a second connection tube 31, a third connection tube 41, a fourth connection tube 141, a supporting device 15, a double-balloon catheter device 5, a first balloon 6, an intermediate balloon 13, and a second balloon 7; the first balloon liquid injection connection port 2 is connected to the supporting device 15 by the first connection tube 21, the second balloon liquid injection connection port 4 is connected to the supporting device 15 by the third connection tube 41, the guide wire connection port 3 is connected to the supporting device 15 by the second connection tube 31, and the third balloon liquid injection connection port 14 is connected to the supporting device 15 by the fourth connection tube 141; the two ends of the double-balloon catheter device 5 are a first end portion 502 and a second end portion 501, respectively, the first end portion 502 is connected to the supporting device 15, and the second end portion 501 is provided with a balloon catheter tip 10; the first balloon 6, the intermediate balloon 13, and the second balloon 7 are disposed at the double-balloon catheter device 5, the intermediate balloon 13 is located between the first balloon 6 and the second balloon 7, and the second balloon 7 is disposed adjacent to the balloon catheter tip 10, and the first balloon 6 is located between the first end portion 502 and the intermediate balloon 13.

Referring to FIG. 7 and FIG. 8, the double-balloon catheter device 5 shown in FIG. 7 is provided sequentially with a first balloon 6, an intermediate balloon 13, and a second balloon 7, and a first balloon tantalum mark 8 is provided on a side of the first balloon 6 close to the second balloon 7, a second balloon tantalum mark 9 is provided on a side of the second balloon 7 remote from the first balloon 6, and the second end portion 501 of the double-balloon catheter device 5 is provided with a balloon catheter tip 10; the double-balloon catheter device 5 is further provided with a liquid outlet 12, which is located between the first balloon 6 and the second balloon 7; the first balloon 6 communicates with the first balloon liquid injection connection port 2 through a first balloon liquid injection channel 51 provided in the double-balloon catheter device 5, the second balloon 7 communicates with the second balloon liquid injection connection port 4 through a second balloon liquid injection channel 53 provided in the double-balloon catheter device 5, and the liquid outlet 12 communicates with the guide wire connection port 3 through a guide wire channel 52 provided in the double-balloon catheter device 5; and the intermediate balloon 13 communicates with the third balloon liquid injection connection port 14 through a third balloon liquid injection channel 54 provided in the double-balloon catheter device 5.

Finally, it should be noted that the embodiments described above are merely intended to illustrate the technical solutions of the present disclosure, but not intended to limit the present disclosure. Although the present disclosure has been described in detail with reference to the foregoing embodiments, it should be understood by those of ordinary skill in the art that the technical solutions disclosed in the foregoing embodiments may still be modified, or some or all of the technical features thereof may be replaced with equivalents; and such modifications or replacements will not cause the essence of the corresponding technical solutions to depart from the scope of the technical solutions of the embodiments of the present disclosure.

INDUSTRIAL APPLICABILITY

As described above, the present disclosure provides a double-balloon catheter device for gastrointestinal anastomosis, which has a simple structure and can be used in a gastrointestinal anastomosis surgery to serve the function of positioning an EUS needle and determining a target while also serving the function of fixing the proximal small intestine, to ensure no displacement of the proximal small intestine during the next step of puncture from the stomach to the proximal small intestine using an ultrasound endoscope (EUS), thereby guaranteeing successful puncture and successful release of a stent.

What is claimed is:

1. A double-balloon catheter device for gastrointestinal anastomosis, comprising a liquid injection assembly, a double-balloon assembly, an introduction assembly, and a supporting device connecting the liquid injection assembly and the double-balloon assembly,
wherein the liquid injection assembly comprises a first balloon liquid injection connection port, a guide wire connection port, and a second balloon liquid injection connection port;
the double-balloon assembly comprises a double-balloon catheter device and expandable first balloon and second balloon disposed at two ends of the double-balloon catheter device, respectively,
the double-balloon catheter device is provided with a first balloon liquid injection channel, a guide wire channel, and a second balloon liquid injection channel,
the first balloon liquid injection channel has an inlet connected to the first balloon liquid injection connection port and has an outlet connected to a liquid injection port of the first balloon,
the second balloon liquid injection channel has an inlet connected to the second balloon liquid injection connection port and has an outlet connected to a liquid injection port of the second balloon, and the guide wire channel has an inlet connected to the guide wire connection port and has an outlet connected to a liquid outlet provided on the double-balloon catheter device between the first balloon and the second balloon,
the supporting device is connected to a first end portion of the double-balloon catheter device,
the introduction assembly is configured to deliver the double-balloon catheter device into a gastrointestinal tract, the introduction assembly comprises a hose configured to accommodate the double-balloon assembly and the supporting device.

2. The double-balloon catheter device for gastrointestinal anastomosis according to claim 1, wherein the introduction assembly comprises a guide wire, and the hose is configured to accommodate the guide wire.

3. The double-balloon catheter for gastrointestinal anastomosis according to claim 2, wherein the hose is configured to allow a gastroscope to pass therethrough, and is provided with a rapid-exchange connection port allowing the double-balloon catheter device and the guide wire to enter an interior of the hose.

4. The double-balloon catheter for gastrointestinal anastomosis according to claim 2, wherein the first balloon liquid injection connection port, the guide wire connection port, and the second balloon liquid injection connection port are distributed in a misaligned manner inside the hose.

5. The double-balloon catheter for gastrointestinal anastomosis according to claim 4, wherein the guide wire connection port is configured to be connected to an injection device.

6. The double-balloon catheter for gastrointestinal anastomosis according to claim 2, wherein the hose has an outer diameter of a, and the hose has an inner diameter of b,
wherein 9.5 mm≤a≤25 mm;
9 mm≤b≤18 mm.

7. The double-balloon catheter for gastrointestinal anastomosis according to claim 6, wherein a=13 mm.

8. The double-balloon catheter for gastrointestinal anastomosis according to claim 6, wherein b=10.5 mm.

9. The double-balloon catheter for gastrointestinal anastomosis according to claim 1, wherein the double-balloon catheter device is provided with at least one balloon tantalum mark, and the first balloon and/or the second balloon are each correspondingly provided with the balloon tantalum mark.

10. The double-balloon catheter for gastrointestinal anastomosis according to claim 9, wherein the balloon tantalum mark comprises a first balloon tantalum mark and a second balloon tantalum mark, wherein the first balloon tantalum mark is provided on a side of the first balloon close to or remote from the second balloon, and the second balloon tantalum mark is provided on a side of the second balloon close to or remote from the first balloon.

11. The double-balloon catheter for gastrointestinal anastomosis according to claim 10, wherein the first balloon tantalum mark is provided on a side of the first balloon close to the second balloon, the second balloon tantalum mark is provided on a side of the second balloon remote from the first balloon, and the double-balloon catheter device is provided with a balloon catheter tip at its second end portion close to the second balloon.

12. The double-balloon catheter for gastrointestinal anastomosis according to claim 1, wherein an intermediate balloon configured for positioning of puncture is further provided at the double-balloon catheter device between the first balloon and the second balloon, the liquid injection assembly further comprises a third balloon liquid injection connection port, the double-balloon catheter device is further provided with a third balloon liquid injection channel, an inlet of the third balloon liquid injection channel is connected to the third balloon liquid injection connection port, and an outlet of the third balloon liquid injection channel is connected to a liquid injection port of the intermediate balloon.

13. The double-balloon catheter for gastrointestinal anastomosis according to claim 1, wherein the double-balloon catheter device has an outer diameter of c,
wherein 1.5 mm≤c≤4.5 mm.

14. The double-balloon catheter for gastrointestinal anastomosis according to claim 11, wherein c=2.3 mm.

15. The double-balloon catheter for gastrointestinal anastomosis according to claim 1, wherein the first balloon and/or second balloon are configured to be expanded to have an outer diameter between 20 mm and 50 mm.

16. A double-balloon catheter for gastrointestinal anastomosis, comprising: a liquid injection assembly, a supporting device, a double-balloon assembly, and an introduction assembly,
   wherein the liquid injection assembly comprises a first balloon liquid injection connection port, a guide wire connection port, and a second balloon liquid injection connection port, the first balloon liquid injection connection port is connected to the supporting device by a first connection tube, the guide wire connection port is connected to the supporting device by a second connection tube, and the second balloon liquid injection connection port is connected to the supporting device by a third connection tube;
   the double-balloon assembly comprises a double-balloon catheter device as well as a first balloon and a second balloon which are disposed at the double-balloon catheter device and are expandable, and a first end portion of the double-balloon catheter device is connected to the supporting device;
   the double-balloon catheter device is provided with a first balloon liquid injection channel, a guide wire channel, and a second balloon liquid injection channel, the first balloon liquid injection channel has an inlet communicating with the first connection tube and has an outlet communicating with a liquid injection port of the first balloon, the second balloon liquid injection channel has an inlet communicating with the third connection tube and has an outlet communicating with a liquid injection port of the second balloon, and the guide wire channel has an inlet communicating with the second connection tube and has an outlet communicating with a liquid outlet provided on the double-balloon catheter device between the first balloon and the second balloon; and
   the introduction assembly is configured to deliver the double-balloon catheter device into a gastrointestinal tract, the introduction assembly comprises a hose and a guide wire, and the hose is configured to accommodate the guide wire, the double-balloon assembly, and the supporting device.

17. The double-balloon catheter device for gastrointestinal anastomosis according to claim 16, wherein a second end portion of the double-balloon catheter device is provided with a balloon catheter tip, the second balloon is closer to the balloon catheter tip than the first balloon, and the first balloon is located between the first end portion and the second balloon.

18. The double-balloon catheter for gastrointestinal anastomosis according to claim 16, wherein the hose is provided with a rapid-exchange connection port, and the rapid-exchange connection port is configured to allow a gastroscope, the double-balloon catheter device, and the guide wire to enter an interior of the hose.

19. The double-balloon catheter for gastrointestinal anastomosis according to claim 16, wherein a balloon tantalum mark is provided on a side of the first balloon close to or remote from the second balloon, and a balloon tantalum mark is also provided on a side of the second balloon close to or remote from the first balloon.

20. The double-balloon catheter for gastrointestinal anastomosis according to claim 16, wherein an intermediate balloon is further provided at the double-balloon catheter device between the first balloon and the second balloon, the liquid injection assembly further comprises a third balloon liquid injection connection port, the third balloon liquid injection connection port is connected to the supporting device by a fourth connection tube, the double-balloon catheter device is further provided with a third balloon liquid injection channel, an inlet of the third balloon liquid injection channel communicates with the fourth connection tube, and an outlet of the third balloon liquid injection channel communicates with a liquid injection port of the intermediate balloon.

21. A double-balloon catheter for gastrointestinal anastomosis, comprising a liquid injection assembly, a double-balloon assembly, and a supporting device connecting the liquid injection assembly and the double-balloon assembly,
   wherein the liquid injection assembly comprises a first balloon liquid injection connection port, a guide wire connection port, and a second balloon liquid injection connection port;
   the double-balloon assembly comprises a double-balloon catheter device and expandable first balloon and second balloon disposed at two ends of the double-balloon catheter device, respectively,
   the double-balloon catheter device is provided with a first balloon liquid injection channel, a guide wire channel, and a second balloon liquid injection channel,
   the first balloon liquid injection channel has an inlet connected to the first balloon liquid injection connection port and has an outlet connected to a liquid injection port of the first balloon,
   the second balloon liquid injection channel has an inlet connected to the second balloon liquid injection connection port and has an outlet connected to a liquid injection port of the second balloon, and the guide wire channel has an inlet connected to the guide wire connection port and has an outlet connected to a liquid outlet provided on the double-balloon catheter device between the first balloon and the second balloon,
   the supporting device is connected to a first end portion of the double-balloon catheter device, and
   wherein an intermediate balloon configured for positioning of puncture is further provided at the double-balloon catheter device between the first balloon and the second balloon, the liquid injection assembly further comprises a third balloon liquid injection connection port, the double-balloon catheter device is further provided with a third balloon liquid injection channel, an inlet of the third balloon liquid injection channel is connected to the third balloon liquid injection connection port, and an outlet of the third balloon liquid injection channel is connected to a liquid injection port of the intermediate balloon.

\* \* \* \* \*